(12) United States Patent
Hen

(10) Patent No.: US 8,110,208 B1
(45) Date of Patent: Feb. 7, 2012

(54) HEMOSTATIC COMPOSITIONS FOR ARRESTING BLOOD FLOW FROM AN OPEN WOUND OR SURGICAL SITE

(75) Inventor: John Hen, Bradenton, FL (US)

(73) Assignee: Biolife, L.L.C., Sarasota, FL (US)

( * ) Notice: Subject to any disclaimer, the term of this patent is extended or adjusted under 35 U.S.C. 154(b) by 109 days.

(21) Appl. No.: 12/749,275

(22) Filed: Mar. 29, 2010

Related U.S. Application Data

(60) Provisional application No. 61/211,336, filed on Mar. 30, 2009.

(51) Int. Cl.
*A61F 13/00* (2006.01)
*A61F 2/00* (2006.01)
*A61K 9/14* (2006.01)

(52) U.S. Cl. ......... 424/422; 424/423; 424/424; 424/489

(58) Field of Classification Search ........................ None
See application file for complete search history.

(56) References Cited

U.S. PATENT DOCUMENTS

| | | | |
|---|---|---|---|
| 2,163,588 A | 11/1935 | Cornish | |
| 2,366,007 A | 12/1944 | D'Alelio | |
| 2,688,586 A | 9/1954 | Eberl | |
| 2,772,999 A | 12/1956 | Masci et al. | |
| 2,773,000 A | 12/1956 | Masci et al. | |
| 3,206,361 A | 9/1965 | Shelley | |
| 3,284,293 A | 11/1966 | Mohr et al. | |
| 3,328,259 A | 6/1967 | Anderson | |
| 3,463,320 A | 8/1969 | Patterson | |
| 4,265,233 A | 5/1981 | Sugitachi et al. | |
| 4,291,980 A | 9/1981 | Patterson | |
| 4,545,974 A | 10/1985 | Thompson | |
| 4,655,211 A | 4/1987 | Sakamoto et al. | |
| 5,474,782 A | 12/1995 | Winter et al. | |
| 5,484,913 A | 1/1996 | Stilwell et al. | |
| 5,679,372 A | 10/1997 | Shimuzu et al. | |
| 5,692,302 A | 12/1997 | Martin et al. | |
| 5,763,411 A | 6/1998 | Edwardson et al. | |
| 5,800,372 A | 9/1998 | Bell et al. | |
| 5,804,428 A | 9/1998 | Edwardson et al. | |
| 5,874,479 A | 2/1999 | Martin | |
| 5,962,026 A | 10/1999 | Edwardson et al. | |
| 5,981,606 A | 11/1999 | Martin | |
| 5,985,432 A * | 11/1999 | Wang et al. .................. | 428/304.4 |
| 6,187,347 B1 | 2/2001 | Patterson et al. | |
| 6,521,265 B1 | 2/2003 | Patterson | |
| 7,303,759 B2 | 12/2007 | Mershon | |
| 7,435,425 B2 | 10/2008 | Qian et al. | |
| 7,547,446 B2 | 6/2009 | Qian et al. | |
| 2008/0138387 A1 | 6/2008 | Machiraju | |
| 2008/0319476 A1 | 12/2008 | Ward et al. | |
| 2009/0062233 A1 | 3/2009 | Ji et al. | |
| 2009/0098193 A1 | 4/2009 | Cochrum et al. | |
| 2009/0117175 A1 | 5/2009 | Finkielsztein et al. | |
| 2009/0123525 A1 | 5/2009 | Bedard | |
| 2009/0148502 A1 | 6/2009 | Pronovost | |
| 2009/0192429 A1 | 7/2009 | Daniels et al. | |
| 2009/0232877 A1 | 9/2009 | Montes et al. | |
| 2009/0234314 A1 | 9/2009 | Nakamura et al. | |

FOREIGN PATENT DOCUMENTS

WO  WO 2008127287 A2 * 10/2008

* cited by examiner

*Primary Examiner* — Susan Tran
(74) *Attorney, Agent, or Firm* — Charles J. Prescott

(57) ABSTRACT

A hemostatic composition for stopping or decreasing blood flow from an open wound or medical or surgical procedure. Compositions of the invention comprise a mixture of a cationic polymer and a cation exchange material. In one embodiment, the composition comprises a mixture: (1) a high molecular weight copolymer of diallyl dimethyl ammonium chloride (DADMAC) and acrylamide [DADMAC copolymer], and (2) the hydrogen form of a crosslinked, sulfonated polystyrene (hydrogen resin). In an exemplified embodiment, a composition of the invention comprises the mixture of DADMAC copolymer and hydrogen resin provided in a dry powdered form. The compositions of the invention may be applied directly to a wound or treatment site, or they may be incorporated into a wound dressing, such as a bandage. The seal formed at a wound or treatment site treated with the present invention is adhesive and exhibits considerable toughness.

7 Claims, No Drawings

HEMOSTATIC COMPOSITIONS FOR ARRESTING BLOOD FLOW FROM AN OPEN WOUND OR SURGICAL SITE

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to compositions for arresting blood flow from an open wound or surgical site, and particularly to an anhydrous mixture of a cationic polymer and a cationic exchange material and more particularly to a cationic exchange material coated with a cationic polymer.

2. Description of Related Art

In addition to conventional bandages, adhesive means, compresses and the like which are applied with pressure directly against a bleeding open wound, considerable effort has been directed toward the development of chemical agents in various forms that accelerate or enhance the coagulation of blood flowing from an open wound to arrest blood flow. Many of these agents are in the "clotting chain," i.e., fibrinogen, thrombin, Factor VIII and the like. Others are based upon the use of collagens. Edwardson, in U.S. Pat. Nos. 5,763,411, 5,804,428, and 5,962,026, for example, teaches the use of fibrin in conjunction with a solid support and as an enzyme free sealant, and as a solid composition substantially free of catalytic enzymes.

Several patents disclose compositions that promote wound healing in conjunction with a clotting component, including Martin, U.S. Pat. Nos. 5,692,302, 5,874,479, and 5,981,606; Stillwell, U.S. Pat. No. 5,484,913; and Winter et al., U.S. Pat. No. 5,474,782. In U.S. Pat. No. 2,163,588, Cornish teaches a wound pad having very fine fibers carrying a viscous agent and a styptic for arresting and clotting blood flow. Eberl et al., U.S. Pat. No. 2,688,586, teach an improved hemostatic surgical dressing with alginic acid as a clotting agent. Masci et al., U.S. Pat. Nos. 2,772,999 and 2,773,000, also teach hemostatic surgical dressing including a pad and free acid cellulose glycolic acid. A patent for another hemostatic wound dressing is taught by Shelley in U.S. Pat. No. 3,206,361 having an active agent in the form of methylaminoacetocatechol hydrochloride. Likewise, Anderson, in U.S. Pat. No. 3,328,259, discloses a wound dressing containing a film of cellulose glycolic acid ether as the hemostatic agent.

A multitude of other patents, for example Sugitachi et al., U.S. Pat. No. 4,265,233, teach various ready-to-use bandages, pads or other carrying agents containing a hemostatic agents, including Factor VIII, fibrin, thrombin, collagen, polyethylene oxide, epsilon aminocaproic acid (EACA) with calcium chloride, etc. Sakamoto teaches in U.S. Pat. No. 4,655,211 a carrier in the shape of a flake or fiber having thrombin and Factor XIII affixed thereto.

Other patents disclose various fibers capable of inducing clotting. For example, Shimizu et al. in U.S. Pat. No. 5,679,372 teaches absorbable acetocollagen fibers, while Bell, et al., U.S. Pat. No. 5,800,372, discloses a dressing made of microfibrillar collagen and a super absorbent polymer for blood absorption and clotting inducement. U.S. Pat. No. 6,521,265 to Patterson and U.S. Pat. No. 6,187,347 to Patterson et al. disclose an admixture of salt ferrate with a cation exchange material that, when hydrated results in the concentration of blood and reduction of $Fe^{+6}$ to $Fe^{+++}$ to induce clotting.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to hemostatic compositions for stopping or decreasing blood flow from an open wound or a medical or surgical procedure site. Compositions of the invention comprise a mixture of a cationic polymer and a cationic exchange material and particularly to a cationic exchange material coated with a cationic polymer. In one embodiment, a composition of the invention comprises a copolymer of diallyl dimethyl ammonium chloride (DADMAC) and acrylamide (henceforth represented as DADMAC copolymer), and the hydrogen form of a crosslinked, sulfonated polystyrene cation exchange resin (henceforth represented as hydrogen resin). An example of the copolymer of diallyl dimethyl ammonium chloride and acrylamide is known as Merquat 550. Merquat 550 is polyquaternary polymer with a molecular weight of $1.6 \times 10^6$ marketed by Nalco as a component of skin care products. In an exemplified embodiment, a composition of the invention comprises a mixture of DADMAC copolymer and hydrogen resin provided in a dry powdered form. One method of preparing the dried powder form consists of coating the hydrogen resin (either prewetted or dry) with a dilute aqueous solution of Merquat 550 cationic polymer. The water swells the hydrogen resin to its equilibrium absorption capacity of about 80% (for a hydrogen resin crosslinked with 2% divinylbenzene). Its high molecular weight of does not allow Merquat 550 to be absorbed into the hydrogen resin and it stays outside of the resin surface. On thorough drying, the cationic polymer is seen mainly as a coating on the surface of the hydrogen resin when viewed under the optical microscope. The exemplified composition may be applied directly to a wound or treatment site, or it may be incorporated into a wound dressing, such as a bandage or fibrous material. The seal formed with blood or serum at a wound site treated with the present invention is adhesive and exhibits considerable toughness. The subject invention also concerns wound and surgical site dressings and coverings, and methods of using a composition of the invention to stop blood flow and to improve wound healing from an open wound or treatment site.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein may be combined with any and/or all other elements or limitations (individually or in any combination) or any other invention or embodiment thereof disclosed herein, and all such combinations are contemplated with the scope of the invention without limitation thereto.

DETAILED DESCRIPTION OF THE INVENTION

This invention pertains to compositions and methods for stopping or decreasing the blood flow from an open wound or a medical or surgical procedure site as well as materials and methods for wound healing. Compositions of the invention comprise substantially an anhydrous mixture of a cationic polymer and a cationic ion exchange material including a cationic ion exchange material coated with a cationic polymer.

Cationic Polymers

A cationic polymer includes polymers that, because of their molecular weight or monomer composition, are soluble or dispersible to at least 0.01% by weight in distilled water at 25° C. The molecular weight (as measured by Gel Permeation Chromatograpy) of the cationic polymer can range from $1\times10^4$ to $1\times10^8$, preferably from $1\times10^5$ to $1\times10^7$, more preferably from $5\times10^5$ to $2\times10^6$. Water soluble cationic polymers include polymers in which one or more of its constituent monomers are selected from a list of copolymerizable cationic, amphoteric and non-ionic and polar monomers. The cationic polymers of the present invention may be quaternary ammonium salts or amine salts. Preferably the cationic polymers are homopolymers or copolymers where one or more of its constituent monomers are quaternary ammonium salts and amines. Examples of the cationic monomers are: dimethyl amino ethylacrylate methyl chloride quaternary (CAS 44992-01-0), dimethyl amino ethylmethacrylate methyl chloride quaternary, dimethylamino-ethylmethacrylate (CAS 5039-78-1), diallyldimethylammonium chloride (CAS 7398-69-8), methacrylamidopropyl trimethylammonium chloride, N-vinyl pyrrolidinone, vinyl-pyridine, N,N-dimethylaminomethylacrylamide, N,N-dimethylaminomethylmeth-acrylamide, N,N-dimethylaminomethylacrylamide quaternaries, Acryloxy Ethyldimethyl-benzylammonium chloride, ethyleneimine, etc. Generally such copolymers will contain from 1-99 mole percent, preferably 1-70 mole percent and most preferably 2-50 mole percent of the comonomer or comonomers employed. The polymers and copolymers of the invention may be prepared either using conventional solution polymerization techniques or the so-called inverse emulsion polymerization method which utilized polymerization of water-soluble vinyl monomers in the form of water-in-oil emulsions. This technique is described in Vanderhoff, U.S. Pat. No. 3,284,393, the disclosure of which is incorporated herein by reference.

The cationic polymers of this invention may also be cationic derivatives of natural polymers such as polysaccharide, polyquaternium 10 (Cellulose 2-hydroxyethyl 2-[2-hydroxy-3-(trimethylammonio) propoxy]ethyl 2-hydroxy-3-(trimethylammonio)propyl ether chloride (CAS #81859-24-7), starch and their copolymers with cationic synthetic polymers such as polymer s and co-polymers of cationic vinylpyridine or vinyl pyridinium chloride.

A preferred cationic polymer is copolymer of diallyl dimethyl ammonium chloride (DADMAC) and acrylamide (DADMAC copolymer) known in the trade as Merquat including Merquat 550, a polymer of 30 mole % DADMAC and 70 mole % of acrylamide.

Cation Exchange Material

Cation exchangers contemplated within the scope of the invention include water insoluble polymers containing anionic functional groups such as —$SO_3^-$, —$OPO_3^-$, and —$COO^-$. In the practice of this invention, mixtures of insoluble polymers containing different anionic functional groups may be employed. The polymers may be cross-linked. For example, if the polymer is polystyrene, it may be cross-linked with 1% to 10% divinylbenzene. One embodiment of the present invention utilizes an ion exchange resin in the hydrogen ionic form of a crosslinked, sulfonated styrene divinylbenzene copolymer.

Methods for preparing ion exchange resins of the invention are disclosed in U.S. Pat. No. 4,291,980, which was based, at least in part, on the production of spherical beads comprised of copolymer styrene and divinylbenzene as taught in U.S. Pat. Nos. 2,366,007 and 3,463,320. The counter ion in the ion-exchange resin may be any cation in the atomic table. The preferred counter-ions include hydrogen, elements in Groups IA and IIA. While the most preferred cation is hydrogen, mixed cations may be used such as hydrogen and a Group IA element and/or Group IIA element.

In another embodiment, the cation-exchange material may be inorganic rather than organically based. Inorganic cation-exchange materials include, but are not limited to, natural or synthetic zeolites, hydrated alkali-aluminum silicates of the general formula $M_{2/n}O$, $Al_2O_3 \cdot ySiO_2 \cdot wH_2O$ where M represents a group IA or IIA element, n is the cation valence, y is 2 or greater and w is the number of water molecules contained in the channels within the zeolite. In another embodiment, ion exchange celluloses may be used where the functionalities are classified as strong acid, intermediate acid or weak acid. In another embodiment, mixtures of organic based and inorganic based ion exchangers may be used. The most preferred ion-exchange material is the hydrogen form of a crosslinked, sulfonated polystyrene cation exchange resin (hydrogen resin).

Composition of the Invention

In an exemplified embodiment, a composition of the invention comprises mixture of a copolymer of DADMAC and acrylamide, and hydrogen resin provided in a dry powdered form. The method of forming the mixture includes coating the hydrogen resin with an aqueous solution of the copolymer and drying. The composition may be applied directly to a wound or treatment site, or it may be incorporated into a wound or surgical dressing, such as a bandage. The seal or scab formed at a wound or treatment site treated with the present invention is adhesive and exhibits considerable toughness. The compositions of the subject invention may be used to control bleeding, to absorb exudates and to heal wounds. The strong seal formed allows for strong protection of the wound site against contamination, microbial penetration and speeds healing.

Added Compounds

Compositions of the subject invention may also comprise additional optional compounds or agents that provide for increased anti-microbial, absorptive, and/or wound healing properties. In one embodiment, a composition of the invention comprises a cationic polymer, a cationic exchange resin, and a silver compound. Silver compounds include, but are not limited to, silver metal (such as nano-silver); silver chlorides; silver oxides; silver sodium hydrogen zirconium phosphate; and silver/zinc form of Zeolite A.

Additional components of compositions of the present invention may include, for example, one or more of: zinc compounds, manganese compounds, calcium compounds, and/or copper compounds or derivatives thereof. Examples include, but are not limited to, zinc oxide, zinc sulfate, zinc stearate, manganese oxide, manganese sulfate, manganese citrate, calcium oxide, calcium sulfate, calcium citrate, calcium carbonate, cuprous sulfate; alginates, carrageenans, and agars; chitosan; absorption polymers such as cross-linked polyacylates and acylate copolymers; natural and/or synthetic gums, such as guar, arabic, or karaya; oxidized celluloses; starches, such as tapioca; and drugs, such as antibiotics.

Forms

Compositions of the invention may be provided in any suitable form. In one embodiment, a composition of the invention is in a loose, free-flowing powder form. In another embodiment, a composition of the invention is provided in a solid wafer or tablet form. Wafers, tablets, and the like may be prepared using standard methods and materials known in the art. In one embodiment, a wafer or tablet is prepared by compressing a powder composition of the invention under substantial pressure, e.g., 4 to 10 tons. In one embodiment, a wafer or tablet of the invention comprises a binder, such as Carbopol 974 NF or polyvinyl pyrrolidone. The use of suitable binders allows wafers and tablets to be prepared at lower pressures. The wafer or tablet may be applied directly to a wound or treatment site or the wafer or tablet may be broken up or crushed into smaller pieces or powder for application to a site. Wafers and tablets may be provided in bulk form or they may be individually packaged. Compositions of the invention are preferably stored under substantially anhydrous conditions and preferably applied as a dry dressing.

Methods of Use

The subject invention also concerns methods of using a composition of the invention to stop blood flow from an open wound or surgical or medical treatment site. In one embodiment, a composition of the invention in dry powder form is applied directly to a wound from which blood or other bodily fluids are flowing. In one embodiment, a wound or treatment site treated with a composition of the invention is subsequently covered with a suitable wound covering or dressing. In another embodiment, a wound covering or dressing is impregnated or coated with or contains composition of the invention and the covering or dressing is applied to the wound. Thus, the present invention may also be practiced in conjunction with wound coverings, dressings, and protective materials, such as BAND-AIDS, bandages, cotton gauze, absorptive pads, and the like.

Treatment Coverings

The subject invention also concerns wound and surgical site treatment coverings, dressings, and the like. In one embodiment, a dressing of the invention comprises a pad that contains a composition of the invention within and/or on the surface of the pad. In a specific embodiment, the pad is composed of porous foam that is sufficiently open to allow a free flow of powder to fill the voids in the porous foam. The open voids may either be random (like a foam air conditioning filter) or organized into tunnels. The tunnels may keep compositions from mixing until needed. The tunnels may be round holes or geometric shapes. Around the perimeter of the randomly open foam a less porous border may be used to contain the composition. The pad may be designed so that lateral pressure may compress the foam or tunnels and hold the composition in place for inverted application.

In another embodiment, a dressing of the invention comprises a pad with fibers perpendicularly oriented to the plane of the pad, wherein the fibers may hold and release a composition of the present invention. The dressing may be provided with or without an integrated foam or fabric or substrate backing. The dressing may be pre-loaded with a composition of the present invention. The dressing may be of a design wherein the fibers remain attached to the dressing during and/or after application to a wound or surgical site.

In one embodiment, a wound dressing of the invention comprises a flocked pad wherein the pad has a foam (e.g., polyurethane) portion and a flocked fibers portion. In one embodiment, the foam portion is a porous foam as described above. In this embodiment, a composition of the invention may be loaded onto the side of the foam opposite that of the fibers and the composition could then travel or flow through the foam and onto the fibers. The fibers may be attached to the foam portion and may be made, for example, out of calcium alginate. The fibers may be a woven or non-woven material. The fibers may be composed of any suitable material such as cotton, wool, etc. In one embodiment, the fibers are composed of a velvet fabric. The fibers may be coated or flocked with a polyacrylate composition. Optionally, the fibers may be composed of dissolvable material (e.g., polyvinyl alcohol) or a biodegradable material (e.g., starch, calcium alginate, polysaccharides, etc.). In one embodiment, the fibers may be composed of a material that may dissolve in a solution, such as a saline solution. In another embodiment, the fibers themselves do not dissolve in solution but are attached to the pad portion via a substance or material that itself may dissolve in solution. This permits a solution to be contacted with a dressing of the invention that has been applied to a site where blood has coagulated and formed a scab, wherein the fibers dissolve or the attachment dissolves and the pad portion of the dressing may then be easily removed without ripping the scab off the wound.

Another embodiment of the dressing includes an "island" dressing wherein the dressing has a hollow or open center area that is positioned over the wound or medical treatment site and wherein a composition of the invention may be applied once the dressing is applied to the wound or treatment site. Alternatively, the dressing may have a composition of the invention pre-loaded into the center of the dressing prior to application to a wound or treatment site, wherein the composition is held in place in the dressing by a suitable material that may be removed prior to use of the dressing or that may dissolve in solution or upon contact with blood at the wound or treatment site.

The island dressing may be of any suitable size, and shape, and thickness appropriate for the wound site or medical procedure being performed. Preferably, the hollow center portion of the dressing where the composition of the invention is to be applied is larger in diameter and/or circumference than the wound site or procedural site being treated. The dressing may be circular, oval, square, rectangular, diamond, trapezoid, triangular, or any other shape, including irregular shapes. The dressing may be composed of any suitable material including, but not limited to, foam, cork, plastic, woven fiber, compressed cotton, and paper materials.

In another embodiment, a dressing of the invention comprises a pouch or other container that contains a composition of the invention and wherein at least one surface of the pouch or container that contacts the wound or treatment site is dissolvable or biodegradable in blood, bodily fluids, exudates, or other liquids or solvents. In one embodiment, a pouch may be composed of paper or paper blends, polypropylene, or polyvinyl alcohol.

In a further embodiment, a composition of the invention is provided in a paste formulation. Carriers that may be used in a paste of the invention include long chain hydrocarbons that impart body, such as, for example, mineral oil and petroleum jelly.

The dosage or amount of a composition of the invention to be typically administered or applied to a site may be readily determined by an ordinarily skilled clinician and will be dependent on various factors, such as the size and type of wound or the surgical or medical procedure being performed, the amount of blood or fluid present in the wound or treatment site, and physical characteristics of the patient, as well as other drugs or treatments the patient is receiving.

All patents, patent applications, provisional applications, and publications referred to or cited herein are incorporated by reference in their entirety, including all figures and tables, to the extent they are not inconsistent with the explicit teachings of this specification.

EXAMPLES

Following are examples which illustrate procedures for practicing the invention. These examples should not be construed as limiting. All percentages are by weight and all solvent mixture proportions are by volume unless otherwise noted.

Example 1

Preparation of Hydrogen Resin Coated with Cationic Polymer

The hydrogen form of a 2% divinyl-benzene crosslinked, sulfonated polystyrene cation exchange resin (hydrogen resin) is available in the fully wetted state with 80% by weight of water. The wet resin has an average bead size of 300 microns. The resin was dried in a 120 C oven to 1 to 3% moisture. The bead size of the dry resin shrunk to an average bead size of about 200 microns. The dry resin was ground to an average bead size of 106 microns. Subsequently, the 106 micron ground hydrogen resin was fully wetted with distilled water. Sufficient amounts of a 4% aqueous solution of Merquat 550 (copolymer of 30 mole % PolyDADMAC and 70 mole % acrylamide with a molecular weight of $1.6 \times 10^6$) was added to the wet 106 micron hydrogen resin to make up 0%, 2.5% 5.0 and 7.5% active concentration in hydrogen resin.

After thorough mixing, the wet mixtures were dried at 120° C. to 0% moisture in an AND Moisture Analyzer. The resulting red and translucent dry powder became lighter (cream color) with increasing concentration of the cationic polymer. When viewed under a 70× microscope, the cationic polymer appears as a clear light coating over the resin. Significant clustering of the fine resin particles by themselves and with coarser resin particles were evident particularly as the concentration of cationic polymer increased. Without cationic polymer, there were little or no clustering.

Example 2

Hemostasis Properties of the Addition of Cationic Polymer to Hydrogen Resin

The hemostasis properties were evaluated using the Blood Seal Test described as follows:

A tenth (0.1) of a milliliter (ml) of stabilized bovine blood was spread out evenly on a one inch diameter circular template in a plastic tray. 300 mg of test powder was poured onto the template to cover the circular area. After a specified time of standing (3 minutes and 1.5 minutes), the integrity of the seal (barrier) formed by the blood and test powder was evaluated by scraping with a small spatula. The amount of seal remaining after scraping was measured in an analytical balance. Qualitative readings of the following parameters were made: blood absorption, adhesion of the seal during the scrapping process and % coverage of the seal after scrapping. For adhesion, an excellent rating was assigned where seal cannot be scrapped off with only moderate force. A poor rating was assigned when seal was scrapped off very easily with little force. The test results are presented in Table 1 herebelow.

TABLE 1

Hemostasis Properties

| 3 MINUTE STANDING TIME | | |
|---|---|---|
| sample | Hydrogen Resin (HR) | 2.5% Merquat 550 in HR |
| blood absorption | moderate | very good |
| mg remaining seal | 25 | 46 |
| % coverage | 35 | 38 |
| adhesion | good | very good |
| remaining seal after 10 min | very brittle, easily scrapped off with almost no force | less brittle, scrapped off with moderate force |
| sample | 5.0% Merquat 550 in HR | 7.5% Merquat 550 in HR |
| blood absorption | very good | very good |
| mg remaining seal | 75 | 80 |
| % coverage | 50 | 55 |
| adhesion | very good to excellent | excellent |
| remaining seal after 10 min | not brittle, not easily scrapped off | not brittle, not easily scrapped off |
| 1.5 MINUTE STANDING TIME | | |
| sample | Hydrogen Resin (HR) | 2.5% Merquat 550 in HR |
| blood absorption | moderate | very good |
| mg remaining seal | 12 | 48 |
| % coverage | 25 | 50 |
| adhesion | good | very good |
| remaining seal after 10 min | very brittle, easily scrapped off with almost no force | not brittle, not easily scrapped off |
| sample | 5.0% Merquat 550 in HR | 7.5% Merquat 550 in HR |
| blood absorption | very good | very good |
| mg remaining seal | 58 | 62 |
| % coverage | 50 | 50 |
| adhesion | very good to excellent | very good to excellent |
| remaining seal after 10 min | not brittle, not easily scrapped off | not brittle, not easily scrapped off |

Note:
"mg remaining seal" is a qualitative measure of seal thickness at the same coverage; thickness increases as mg of remaining seal increases.

Table 1 summarizes the hemostasis study. At 3 minutes standing time, hydrogen resin by itself absorbed blood moderately, provided 25 mg of remaining seal and 35% coverage, and good adhesion. However, the remaining seal was so brittle after ten minutes that the seal could be removed simply by tapping the back of the plastic tray. All tested hemostatic properties improved with increasing concentration of Merquat 550 in the hydrogen resin (blood absorption, mg remaining seal, % coverage, adhesion, and reduction or elimination of seal brittleness after ten minutes). The best properties were achieved at the highest cationic polymer concentration. The trend seen at 3 minute standing time was confirmed at half the standing time. The blood seal test was also applied to a 5% Merquat 550 aqueous solution by itself. After 3 minutes of standing, the polymer solution simply diluted the bovine blood and did not appear to lyze or clot the red blood cells. The blood/polymer solution mix was fluid and did not result in a seal.

By themselves, Merquat 550 did not form a blood seal while hydrogen resin formed a very brittle blood seal with acceptable hemostasis property. The incorporation of Merquat 550 into the hydrogen resin gave surprisingly desirable hemostatic properties including significantly improved adhesion and toughness to the blood seal.

Notes: Merquat 550 was sourced from Nalco as a 9% active viscous solution in water. The hydrogen resin was sourced from Dow Chemical.

Example 3

Finger Stick Test

Human Test

An auto-Lancet was used to obtain capillary blood sample. The two drops of drawn blood were left on the finger. About 50 mg of test powder was poured on top of the blood. The spot was compressed with a gloved finger from the other hand for 30 seconds. Excess powder was discarded. After 8 minutes, the ease with which the blood seal may be rubbed off with a spatula was qualitatively assessed. The seal formed by hydrogen resin was moderately thick and was easily and completely removed with the spatula. Unexpectedly, the seal formed by the composition of 5% Merquat 550 in hydrogen resin was very strong and adhesive and difficult to remove.

Example 4

Hydrogen Resin with Finer Particle Size

Blood seals formed from hydrogen resin is strongly influenced by particle size. The finer particle size (40 micron average) produced a thinner seal than the 106 micron material. Finger stick test was conducted to compare the 40 micron hydrogen resin by itself and the same hydrogen resin containing 5% Merquat 550. The seal from the 40 micron hydrogen resin was thinner than the seal from the 106 micron hydrogen resin (Example 3). The strength of both seals was poor and was easily scrapped off. The seal formed by adding 5% Merquat 550 to the fine particle size hydrogen resin was excellent in adhesion and strength. This seal stayed strong for overnight, after which it was easily removed by flushing with water.

Example 5

In Vitro Hemostasis Test

The In Vitro Hemostasis Test Apparatus was used to evaluate the efficiency to control bleeding of hemostatic dressings. The test provides a measure of seal strength as defined by pressure at which a dressing fails. The apparatus consists of a pump forcing air up at the point of the Test Block that has a 5/32" hole drilled into it. The hole was covered with an aluminum disk to prevent powder from filling the hole. Bovine blood was spread on top of the disk. Test powder was poured into the blood and a 200 gram weight placed on top of the powder pile. After 60 seconds, the weight was removed, and air was allowed to come through the hole at a programmed rate of increase in pressure. The pressure at which the seal fails is recorded. Two compositions were tested: 106 micron hydrogen resin by itself and the hydrogen resin containing 6% Merquat 550. The results are shown below:

TABLE 2

In Vitro Hemostasis Test

| Test Dressing | Failure Pressure (mm Hg) |
| --- | --- |
| 106 micron hydrogen resin | 56 |
| 6% Merquat 550 in hydrogen resin | 75 |

The addition of 6% Merquat 550 increased the failure pressure of the blood seal 34% from 56 mm to 75 mm Hg.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A hemostatic composition for stopping or decreasing blood flow from an open wound or medical or surgical procedure consisting of:
   a mixture of a cationic polymer and a cation exchange material, wherein said cationic polymer is a homopolymer or a copolymer wherein a constituent monomer thereof is selected from the group consisting of dimethyl amino ethyl methacrylate methyl chloride quaternary, diallyldimethylammonium chloride, methacrylamidopropyl trimethylammonium chloride, N,N-dimethylaminomethylacrylamide quaternaries, and acryloxy ethyldimethylbenzylammonium chloride.

2. A hemostatic composition as set forth in claim 1, wherein:
   said cation exchange material is coated with said cationic polymer.

3. A hemostatic composition as set forth in claim 1, wherein:
   said cationic polymer is a high molecular weight copolymer of diallyl dimethyl ammonium chloride (DADMAC) and acrylamide [DADMAC copolymer].

4. A hemostatic composition as set forth in claim 1, wherein:
   said cation exchange material is a hydrogen form of a crosslinked sulfonated polystyrene.

5. A hemostatic composition as set forth in claim 1, wherein:
   said cation exchange material is an ion exchange resin.

6. A hemostatic composition as set forth in claim 5, wherein:
   said ion exchange resin is a counter ion taken from the group of elements consisting of Group IA and Group IIA of the atomic table.

7. A hemostatic composition as set forth in claim 1 wherein said cationic polymer is selected from the group consisting of:
   cationic polysaccharide, cationic starches and cellulose 2-hydroxyethyl 2-[2-hydroxy-3-(trimethylammonio) propoxy]ethyl 2-hydroxy-3-(trimethylammonio) propyl ether chloride (Polyquaternium 10).

* * * * *